(12) United States Patent  
Benet-Buchholz et al.

(10) Patent No.: US 9,309,186 B2
(45) Date of Patent: Apr. 12, 2016

(54) POLYMORPHIC FORM OF A LONG-ACTING BETA-2 ADRENOCEPTOR AGONIST

(71) Applicant: Laboratorios Lesvi S.L., Barcelona (ES)

(72) Inventors: Jordi Benet-Buchholz, Tarragona (ES); Jordi Cerón Bertran, Tarragona (ES); Glòria Freixas Pascual, Tarragona (ES); Pere Dalmases Barjoan, Barcelona (ES); Isabel Navarro Muñoz, Barcelona (ES)

(73) Assignee: LABORATORIOS LESVI S.L., Barcelona (ES)

( * ) Notice: Subject to any disclaimer, the term of this patent is extended or adjusted under 35 U.S.C. 154(b) by 0 days.

(21) Appl. No.: 14/385,069

(22) PCT Filed: Mar. 12, 2013

(86) PCT No.: PCT/GB2013/050605
§ 371 (c)(1),
(2) Date: Sep. 12, 2014

(87) PCT Pub. No.: WO2013/136061
PCT Pub. Date: Sep. 19, 2013

(65) Prior Publication Data
US 2015/0087715 A1 Mar. 26, 2015

Related U.S. Application Data

(60) Provisional application No. 61/609,505, filed on Mar. 12, 2012.

(51) Int. Cl.
*C07C 231/24* (2006.01)
*C07C 231/16* (2006.01)
*C07C 233/43* (2006.01)

(52) U.S. Cl.
CPC .............. *C07C 233/43* (2013.01); *C07C 231/16* (2013.01); *C07C 231/24* (2013.01); *C07B 2200/13* (2013.01)

(58) Field of Classification Search
None
See application file for complete search history.

(56) References Cited

U.S. PATENT DOCUMENTS 6,472,563 B1 10/2002 Tanoury et al.

*Primary Examiner* — Yevegeny Valenrod
(74) *Attorney, Agent, or Firm* — Stites & Harbison, PLLC; Terry L. Wright

(57) ABSTRACT

New polymorphic form of a long-acting beta-2 adrenoceptor agonist A new polymorphic form of arformoterol tartrate, designated as form D, is provided and which is characterized by at least one of the following: (i) a powder X-ray diffraction pattern having peaks at approximately 6.8, 13.3, 13.6, 3.8, 14.1, 18.2, 18.7, 20.0±0.2 degrees two theta; or (ii) a DSC thermogram showing an endothermic peak with an onset at approximately 19-120° C., and a maximum at approximately 129-131° C., followed by an exothermic peak with a maximum at approximately 137-138° C.; wherein the DSC thermogram of form D has a further endothermic peak with an onset at approximately 168-170° C.1 Processes for preparing the new polymorphic form, uses thereof and intermediates for the preparation thereof, are also provided.

19 Claims, 3 Drawing Sheets

POLYMORPHIC FORM OF A LONG-ACTING BETA-2 ADRENOCEPTOR AGONIST

FIELD OF THE INVENTION

This invention relates to a new polymorphic form of a long-acting beta-2 adrenoceptor agonist, arformoterol tartrate. In addition, the invention relates to intermediates in the preparation of the new polymorphic form, processes for obtaining the new polymorphic form, and compositions and uses thereof.

BACKGROUND OF THE INVENTION

Formoterol, (+/−)N-[2-hydroxy-5-[1-hydroxy-2-[[2-(4-methoxyphenyl)-1-methylethyl]amino]ethyl]phenyl]formamide, is a highly potent and $\beta_2$-selective adrenoceptor agonist having a long lasting bronchodilating effect when inhaled. It is represented by the following structural formula:

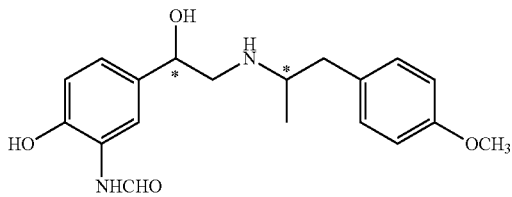

Formoterol was first disclosed in Japanese patent application 13121 (equivalent to U.S. Pat. No. 3,994,974), wherein formoterol is synthesised by N-alkylation using a phenacyl bromide.

Formoterol has two chiral centres, each of which can exist in two different configurations. This results in four different combinations: (R,R), (S,S), (S,R) and (R,S). Formoterol is commercially available as a racemic mixture of 2 enantiomers (R,R) and (S,S) in a 1:1 ratio. The generic name formoterol always refers to its racemic mixture. Trofast et al. (Chirality, 1, 443, 1991) reported on the potency of these isomers, showing a decrease in the order of (R,R)>(R,S)≥(S,R)>(S,S). The (R,R) isomer, also known as arformoterol, being 1000 fold more potent than the (S,S) isomer.

Arformoterol is commercialised by Sepracor as a tartrate salt under the brand name Brovana®. The chemical name for arformoterol tartrate is N-[2-hydroxy-5-[(1R)-1-hydroxy-2-[[(1R)-2-(4-methoxyphenyl)-1-methylethyl]amino]ethyl]phenyl]formamide, (2R,3R)-2,3-dihydroxybutanedioate (1:1 salt), and it is represented by the following structural formula:

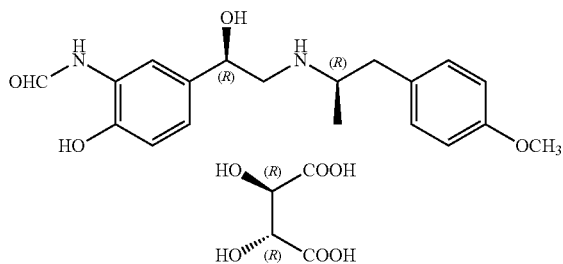

Various processes for the preparation of formoterol, its enantiomers, related compounds, and their pharmaceutically acceptable salts are disclosed in U.S. Pat. Nos. 3,994,974; 5,434,304; 6,268,533 and 6,472,563; Chem. Pharm. Bull. 26, 1123-1129 (1978); Chirality 3, 443-450 (1991); Drugs of the Future 2006, 31(11), 944-952; and WO 2008/035380A2. U.S. Pat. No. 6,268,533 describes salts of arformoterol and a method to produce them; amongst these salts L-tartrate was used to produce R,R-formoterol L-tartrate (hereinafter referred to as arformoterol tartrate). U.S. Pat. No. 6,268,533 further discloses polymorphic forms of arformoterol tartrate referred to as P1 and P2, characterized by Differential Scanning calorimetry (DSC). Polymorph P1 in pure form exhibits a peak at about 193° C. on DSC and a solubility in water at 25° C. to the extent of 15.4 mg/mL. Polymorph P2 in pure form exhibits a transition peak at about 179° C. on DSC and a solubility in water at 25° C. to the extent of 26.7 mg/mL.

U.S. Pat. No. 6,472,563 discloses a further crystalline polymorph of arformoterol tartrate, designated as "polymorph C", and which is reported to be useful for the preparation of highly pure "form A" of arformoterol. U.S. Pat. No. 6,472,563 renamed the polymorphs P1 and P2 of U.S. Pat. No. 6,268,533 as "polymorph A" (i.e. form A) and "polymorph B", respectively. The XRPD peaks and the FTIR spectrum for the polymorphic forms A, B and C are also disclosed in U.S. Pat. No. 6,472,563.

Polymorphs are different crystalline forms of the same pure substance in which the molecules have different spatial configurations relative to each other in the solid state. In accordance with regulatory requirements of the U.S. and other countries, e.g. the FDA's Good Manufacturing Practice ("GMP") requirements, when preparing pharmaceutical compositions containing active ingredients for administration to mammals, there is a need to produce crystalline forms, or polymorphs, which are as pure and as stable as possible. Differences in the chemical and physical properties of polymorphic forms of an active ingredient such as melting point, chemical reactivity and apparent solubility can have a direct effect on the ability to process and/or manufacture the active ingredient and its pharmaceutical compositions, as well as on its stability, dissolution and bioavailability.

Arformoterol tartrate is commercialised as a sterile, clear and colourless aqueous solution for inhalation. Therefore, it is desirable to develop a pure and stable polymorphic form of arformoterol tartrate, which shows reproducibly uniform crystalline form and high solubility, which results in better properties for use in pharmaceutical preparations, particularly in the preparation of liquid pharmaceutical compositions. The preparation of new polymorphic forms and solvates of pharmaceutically useful compounds also provides a new opportunity to improve the performance characteristics of pharmaceutical products and enlarges the repertoire of materials that formulation scientists have available for designing, for example, a pharmaceutical dosage form of a drug with a targeted release profile or other desired characteristic.

BRIEF DESCRIPTION OF THE INVENTION

Thus, in a first aspect of the present invention, there is provided a new polymorphic form of arformoterol tartrate, referred to as form D and defined as herein.

The inventors of the present invention have surprisingly found that arformoterol tartrate can further exist in a new polymorphic form, referred to herein as form D. The new form D shows high purity, good stability and high solubility in water, which makes it suitable for pharmaceutical formulation and in particular for liquid pharmaceutical formulations A second aspect of the present invention relates to a new acetonitrile solvate of arformoterol tartrate. This may be used as an intermediate in the preparation of arformoterol tartrate form D.

A third aspect of the present invention relates to a process for preparing the acetonitrile solvate of arformoterol tartrate of the invention from other polymorphic forms of arformoterol tartrate or mixtures thereof.

A fourth aspect of the present invention relates to a process for preparing arformoterol tartrate form D, from the acetonitrile solvate of arformoterol tartrate of the invention.

A fifth aspect of the present invention relates to a process for preparing arformoterol tartrate form D, from other polymorphic forms of arformoterol tartrate or mixtures thereof.

A sixth aspect of the present invention relates to a process for preparing arformoterol tartrate form D, from arformoterol base.

A seventh aspect of the present invention relates to the use of the acetonitrile solvate of the invention in the preparation of arformoterol tartrate form D.

An eighth aspect of the present invention relates to mixtures of form D and polymorph A of arformoterol tartrate.

A ninth aspect of the present invention relates to a process for the preparation of mixtures of form D and polymorph A of arformoterol tartrate A tenth aspect of the present invention relates to a pharmaceutical composition comprising arformoterol tartrate form D, or a mixture of form D and polymorph A of arformoterol tartrate, and at least one pharmaceutically acceptable excipient. The composition may be in liquid form (e.g. a solution or suspension), or a solid form (e.g. powder for inhalation).

In compositions according to the tenth aspect and containing a mixture of form D and polymorph A of arformoterol tartrate, the composition may be such that the percentage by weight of form D is at least 30% (w/w), preferably from 40% to 90% (w/w), more preferably form 50% to 80% (w/w) relative to the total weight of form D and polymorph A.

An eleventh aspect of the invention relates to arformoterol tartrate form D, a mixture according to the eighth aspect; or a pharmaceutical composition according to the tenth aspect, for use in therapy. A twelfth aspect relates to form D, a mixture according to the eighth aspect, or a pharmaceutical composition according to the tenth aspect, for use as a bronchodilator.

A thirteenth aspect of the invention relates to a method of effecting bronchodilation in a subject in need thereof, the method comprising administering to the subject a therapeutically effective amount of arformoterol tartrate form D, or a mixture of form D and polymorph A of arformoterol tartrate, or a composition according to the tenth aspect.

DEFINITIONS

Figure 1:
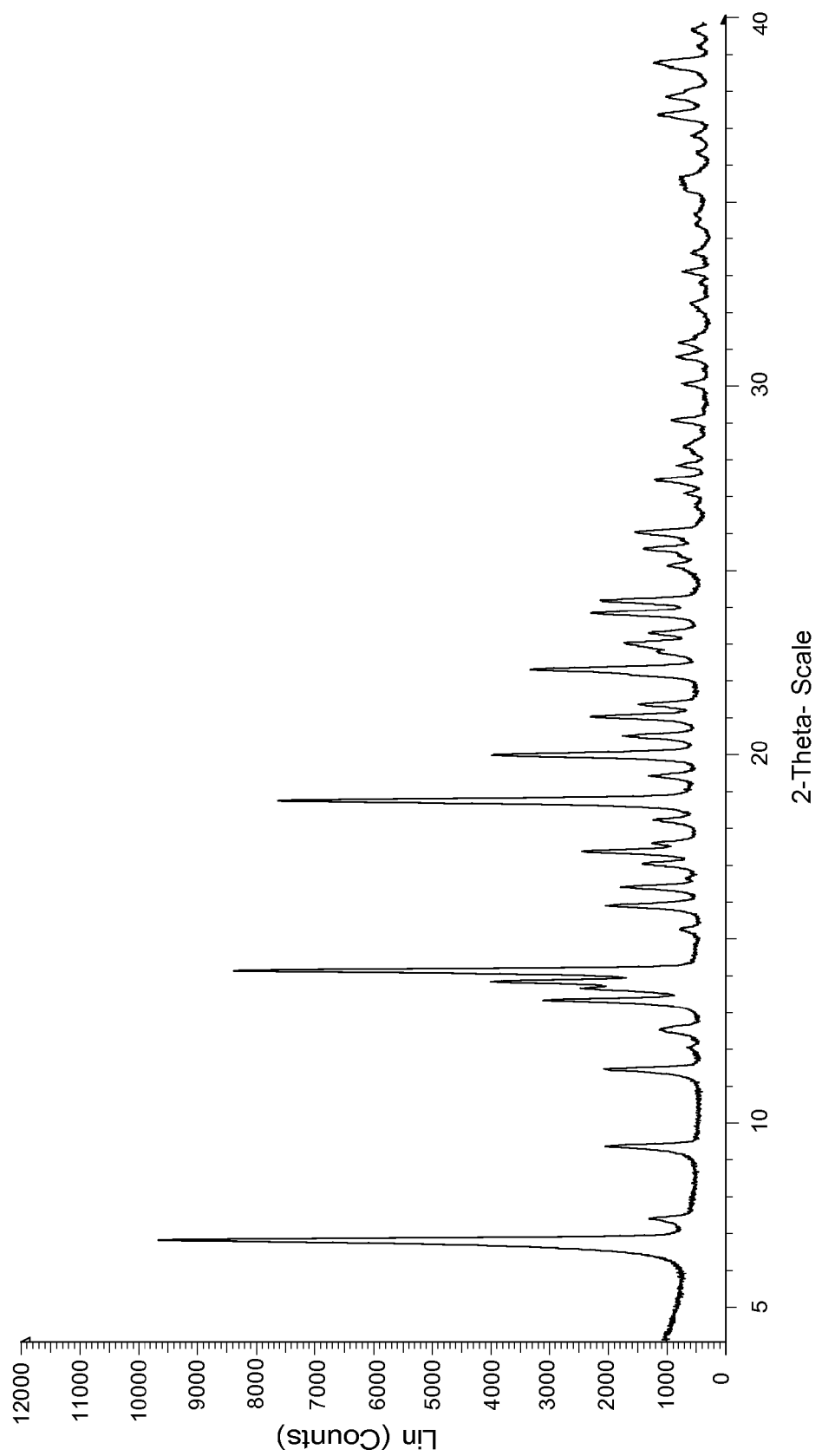
FIG. 1 shows the powder X-ray diffraction pattern (PXRD) of polymorph D of arformoterol tartrate.

The term "interplanar distance" as used herein (and referred to as 'd value') refers to the spacing (in Å) between the planes in the arformoterol tartrate crystal lattice; "crystal lattice" is defined as the array of periodic and repeating arrangements of atoms that are found in crystalline solids.

The term "inlet air pressure" as used herein refers to the pressure exerted by an input stream of air.

The term "particle size distribution" (or "PSD") as used herein refers to the relative percentages by volume of each of the different size fractions of a particulate matter. The particle size distributions of the present application can be measured using laser light diffraction equipment, such as a Malvern Mastersizer® 2000. Particle size is determined by measuring the angular distribution of laser light scattered by a homogeneous suspension of particles. The size distribution is determined from the light scattering data using the theory of light scattering developed by Gustav Mie. Other types of equipment are also suitable to determine particle size distribution. Laser light diffraction results may be expressed by $d_{10}$, $d_{50}$, and/or $d_{90}$ values, which are based on a volume distribution. The term "dx", as used herein, means that x % of the particles in a composition (based on volume) have a diameter equal to or below a specified d value. For example, a $d_{50}$ of 100 μm means that 50% by volume, of the particles, have a diameter equal to or below 100 μm.

DETAILED DESCRIPTION OF THE INVENTION

According to the first aspect, the present invention relates to a polymorphic form of arformoterol tartrate, referred to as form D, and which is characterized by at least one of the following:
(i) a powder X-ray diffraction (PXRD) pattern having peaks at approximately 6.8, 13.3, 13.6, 13.8, 14.1, 18.2, 18.7, 20.0±0.2 degrees two theta (i.e. Bragg's angle); or
(ii) a DSC thermogram showing an endothermic peak with an onset at approximately 119-120° C., and a maximum at approximately 129-131° C., followed by an exothermic peak with a maximum at approximately 137-138° C.; wherein the DSC thermogram of form D has a further endothermic peak with an onset at approximately 168-170° C.

Arformoterol tartrate form D of the present invention can be obtained in 100% ee (enantiomeric purity). Arformoterol tartrate form D of the present invention shows a high chemical purity, containing as low as 0.3% of total impurities, as determined by HPLC. In addition, the arformoterol tartrate form D of the present invention, contains an amount of the degradation impurity (R)-1-(3-amino-4-hydroxyphenyl)-2-[[(1R)-2-(4-methoxyphenyl)-1-methylethyl]amino]ethanol equal or less than 0.2%, as determined by HPLC. Said arformoterol form D remains stable and shows no colour variation under temperatures between 5 and 30° C. and atmospheric, vacuum or inert pressures. Said arformoterol tartrate form D also remains polymorphically and chemically stable and shows no colour variation after at least 6 months of storage under vacuum at 25° C.±2° C. temperature and 60%±5% Relative Humidity (RH), and/or at 40° C.±2° C. temperature and 75%±5% Relative Humidity (RH). The present inventors have also found that arformoterol tartrate form D does not show polymorphic changes when subjected to grinding.

The arformoterol tartrate form D of the present invention has a particle size distribution $d_{50}$ equal to or less than 100 μm, preferably less than 50 μm, more preferably less than 20 μm, still more preferably less than 10 μm and most preferably less than 5 μm.

In a particular embodiment of the first aspect, the arformoterol tartrate form D has a powder X-ray diffraction pattern further comprising one or more additional peaks at approximately 7.4, 15.9, 25.1 and 25.8±0.2 degrees two theta.

In one embodiment of the first aspect, the arformoterol tartrate form D has a powder X-ray diffraction pattern, characterised by the interplanar distance values shown below:

| Angle 2θ (°) (±0.2) | d value (Å) |
|---|---|
| 6.8 | 13.01 |
| 13.3 | 6.65 |
| 13.6 | 6.49 |
| 13.8 | 6.40 |
| 14.1 | 6.27 |
| 18.2 | 4.87 |
| 18.7 | 4.73 |
| 20.0 | 4.44 |

In a particular embodiment of the first aspect, the arformoterol tartrate form D has a powder X-ray diffraction pattern further comprising one or more additional interplanar distance values shown below:

| Angle 2θ (°) (±0.2) | d value (Å) |
|---|---|
| 7.4 | 11.99 |
| 15.9 | 5.58 |
| 25.1 | 3.54 |
| 25.8 | 3.45 |

In one example of the first aspect, the PXRD pattern of the arformoterol tartrate form D can be depicted substantially as in FIG. 1.

In a particular embodiment of the first aspect, the arformoterol tartrate form D of the present invention shows substantially no weight loss before decomposition. Decomposition is observed at temperatures over 167° C.

In another particular embodiment of the first aspect, the arformoterol tartrate form D of the present invention may contain residual non-solvated acetonitrile in an amount equal to or less than 1% (w/w), preferably in an amount equal to or less than 0.5% (w/w), more preferably in an amount equal to or less than 0.2% (w/w), even more preferably in an amount equal to or less than 0.1% (w/w).

The arformoterol tartrate form D of the present invention may exhibit a solubility in water, measured at 25 degrees C., of between 38 and 83 mg/ml.

A second aspect of the present invention relates to an acetonitrile solvate of arformoterol tartrate, characterised by at least one of the following:
(i) a powder X-ray diffraction pattern showing the following peaks at approximately 6.5, 13.7, 17.9, 18.4, 20.3, 21.6, 24.6 and 24.8±0.2 degrees two theta; or
(ii) a DSC thermogram showing an endothermic peak with an onset at approximately 124-125° C., and a maximum at approximately 134-136° C., followed by an exothermic peak with a maximum at approximately 140-141° C.; wherein the DSC thermogram of form D has a further endothermic peak with an onset at approximately 170-172° C.

The solvate of the second aspect may be used as an intermediate in the preparation of arformoterol tartrate form D.

In a particular embodiment of the second aspect, the acetonitrile solvate of arformoterol tartrate has a powder X-ray diffraction pattern further comprising one or more additional peaks at approximately 13.2, 16.6, 19.2, 23.3, and 25.1±0.2 degrees two theta.

In one embodiment of the second aspect, the acetonitrile solvate of arformoterol tartrate has a powder X-ray diffraction pattern, characterised by the interplanar distance values shown below:

| Angle 2θ (°) (±0.2) | d value (Å) |
|---|---|
| 6.5 | 13.66 |
| 13.7 | 6.46 |
| 17.9 | 4.95 |
| 18.4 | 4.81 |
| 20.3 | 4.37 |
| 21.6 | 4.10 |
| 24.6 | 3.62 |
| 24.8 | 3.59 |

In a particular embodiment of the second aspect, the acetonitrile solvate of arformoterol tartrate has a powder X-ray diffraction pattern further comprising one or more additional interplanar distance values shown below:

| Angle 2θ (°) (±0.2) | d value (Å) |
|---|---|
| 13.2 | 6.72 |
| 16.6 | 5.32 |
| 19.2 | 4.62 |
| 23.3 | 3.82 |
| 25.1 | 3.54 |

In a preferred embodiment of the second aspect, the acetonitrile solvate of arformoterol tartrate contains solvated acetonitrile in an amount between 0.2 and 5% (w/w), preferably in an amount between 1.6 and 4.1% (w/w), more preferably in an amount between 2 and 4% (w/w). The acetonitrile solvate of arformoterol tartrate may contain residual non-solvated acetonitrile in an amount equal to or less than 1% (w/w), preferably in an amount equal to or less than 0.5% (w/w), more preferably in an amount equal to or less than 0.2% (w/w), even more preferably in an amount equal to or less than 0.1% (w/w).

Figure 2:
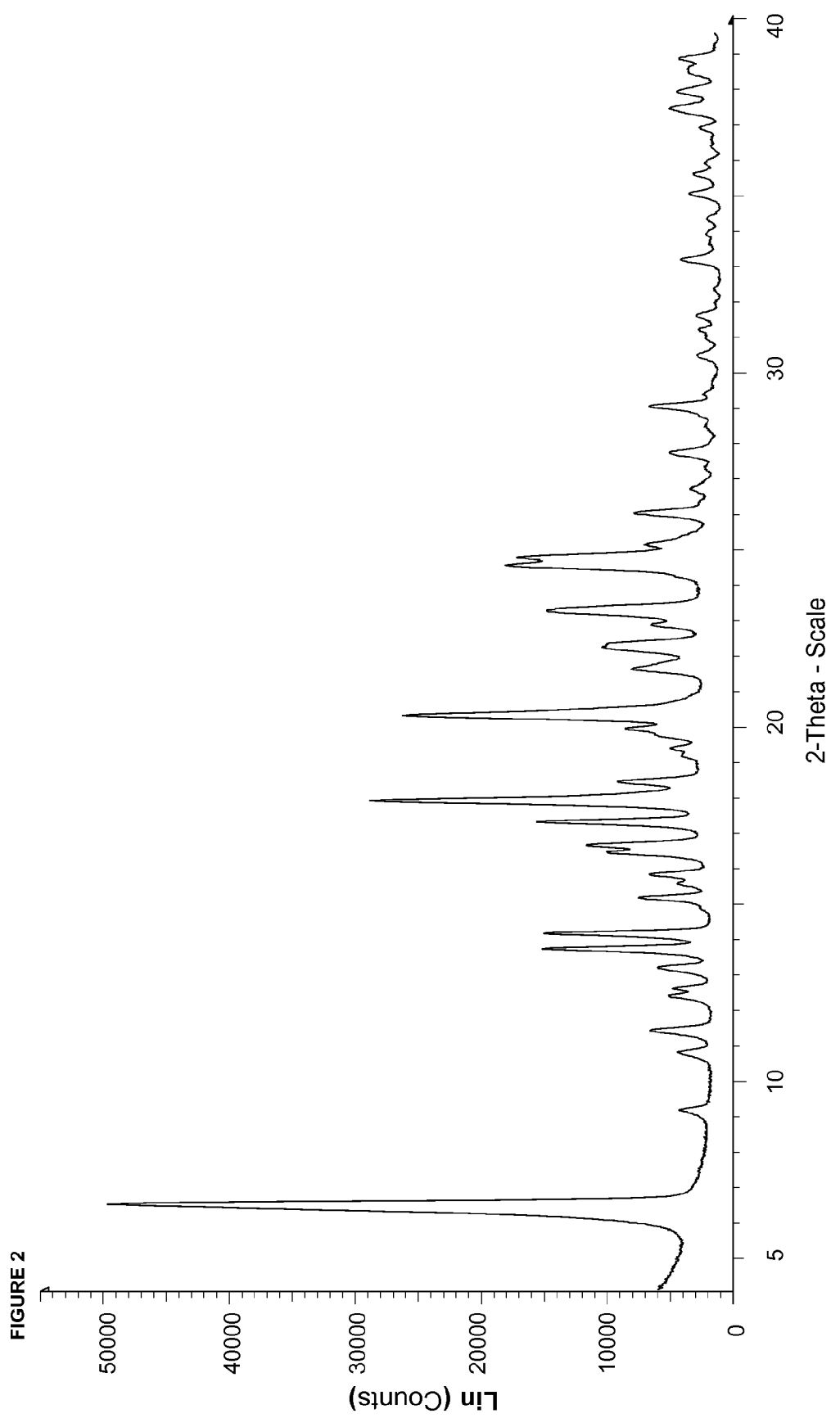
FIG. 2 shows the powder X-ray diffraction pattern (PXRD) of the acetonitrile solvate of arformoterol tartrate of the invention.

In one example of the second aspect, the PXRD pattern of the acetonitrile solvate of arformoterol tartrate can be depicted substantially as in FIG. 2.

A third aspect of the present invention relates to a process for preparing the acetonitrile solvate of arformoterol tartrate of the second aspect from other polymorphic forms of arformoterol tartrate or mixtures thereof, the process comprising the steps of:
a) providing a mixture of arformoterol tartrate and a solvent selected from an alcohol, water and mixtures thereof, at a temperature between 60 and 70° C.;
b) cooling the mixture obtained in step (a) to a temperature between 50 and 55° C.;
c) adding acetonitrile to the mixture obtained in step (b) until a suspension is obtained;
d) cooling the suspension obtained in step (c) while stirring to a temperature between 10 and 30° C. to obtain a solid; and
e) collecting the crystals obtained in step (d) and drying the crystals under vacuum at a pressure between 0.75 and 40 mm Hg and at a temperature between 20 and 45° C.; or drying the crystals under inlet air pressure and at a temperature between 20 and 45° C., to yield acetonitrile solvate of arformoterol tartrate;
wherein when the solvent used in step in step (a) is a mixture of alcohol and water, the ratio of alcohol/water is between 1:1 and 1:9, preferably between 1:1 and 1:5, more preferably between 1:2 and 1:4.

In a preferred embodiment, the alcohol used in step (a) is selected from methanol, ethanol and isopropanol. In a more preferred embodiment, the alcohol is methanol or ethanol.

In one embodiment of the third aspect, the arformoterol tartrate provided in step (a) can comprise other polymorphic forms (i.e. other than form D) of arformoterol tartrate and mixtures thereof.

In another preferred embodiment of the third aspect, the temperature of the mixture of step (a) is between 60 and 65° C.

In a preferred embodiment of the third aspect, the ratio of solvent used in step (a) to the acetonitrile used in step (c) is at least 1:1, preferably between 1:1 and 1:5, more preferably between 1:2 and 1:4. The ratio of solvent in step (a) to acetonitrile is not critical, although it is preferred that the amount of acetonitrile is greater than the amount of solvent.

In a preferred embodiment of the third aspect, the steps (a) to (d) are performed under inert atmosphere, such as under nitrogen or argon atmosphere. Preferably, they are performed under nitrogen atmosphere.

In a particular embodiment of the third aspect, the drying of step (e) is carried out at a pressure that ranges between 0.75 and 40 mm Hg, preferably between 0.75 and 20 mm Hg, more preferably between 0.75 and 3 mm Hg, most preferably between 1.5 and 2.25 mm Hg; and at a controlled temperature between 20 and 45° C., preferably between 25 and 40° C., more preferably between 30 and 40° C. In another embodiment, the drying of step (e) is carried out under inlet air pressure (atmospheric pressure); and at a controlled temperature between 20 and 45° C., preferably between 25 and 40° C., more preferably between 30 and 40° C.

In a more preferred embodiment of the third aspect of the present invention, the process for preparing the acetonitrile solvate of arformoterol tartrate of the second aspect from other polymorphic forms of arformoterol tartrate or mixtures thereof comprises the steps of:
a) providing a mixture of arformoterol tartrate and an alcohol, at a temperature between 60 and 70° C.;
b) cooling the mixture obtained in step (a) to a temperature between 50 and 55° C.;
c) adding acetonitrile to the mixture obtained in step (b) until a suspension is obtained;
d) cooling the suspension obtained in step (c) while stirring to a temperature between 10 and 30° C. to obtain a solid; and
e) collecting the crystals obtained in step (d) and drying the crystals under vacuum at a pressure between 0.75 and 40 mm Hg and at a temperature between 20 and 45° C.; or drying the crystals under inlet air pressure and at a temperature between 20 and 45° C., to yield acetonitrile solvate of arformoterol tartrate;
wherein the alcohol used in step in step (a) is selected from methanol, ethanol and isopropanol, preferably methanol or ethanol The method according to the third aspect of the present invention is simple, and permits to be obtained an acetonitrile solvate of arformoterol tartrate, which can be used as an intermediate in the preparation of the new arformoterol tartrate form D. Said form D shows a high chemical purity (the level of total impurities is as low as 0.3%, as determined by HPLC), remains stable and shows no colour variation under temperatures between 5 and 30° C. and atmospheric, vacuum or inert pressures. Said arformoterol tartrate form D also remains polymorphically and chemically stable and shows no colour variation after at least 6 months of storage under vacuum at 25° C.±2° C. temperature and 60%±5% Relative Humidity (RH), and/or at 40° C.±2° C. temperature and 75%±5% Relative Humidity (RH).

A fourth aspect of the present invention relates to a process for preparing the arformoterol tartrate form D of the first aspect, from the acetonitrile solvate of arformoterol tartrate of the second aspect, comprising the step of drying the crystals of acetonitrile solvate of arformoterol tartrate, obtained for example as disclosed in the third aspect of the present invention, under inlet air pressure (atmospheric pressure) or under vacuum at a pressure between 0.75 and 40 mm Hg, and at a temperature between 50 and 90° C.

As described in the third aspect, the ratio of alcohol/water used in step (a) thereof, when the solvent used in said step is a mixture of alcohol and water, is between 1:1 and 1:9, preferably between 1:1 and 1:5, more preferably between 1:2 and 1:4. The ratio of alcohol/water between 1:1 and 1:9 leads towards the formation of form D. As the ratio of alcohol to water increases over 1:1 (i.e. the amount of alcohol is greater than the amount of water), mixtures of form D and form A are obtained.

In a particular embodiment of the fourth aspect, the pressure applied during drying, ranges between 0.75 and 40 mm Hg, preferably between 0.75 and 20 mm Hg, more preferably between 0.75 and 3 mm Hg, most preferably between 1.5 and 2.25 mm Hg. In another embodiment, the drying of step (e) is carried out under inlet air pressure (atmospheric pressure).

In a preferred embodiment of the fourth aspect, the drying is carried out at a temperature between 60 and 80° C. In a more preferred embodiment, the temperature is 80° C.

The method according to the fourth aspect of the present invention is simple, and permits the end product (arformoterol tartrate form D) to be obtained in a high chemical purity (the level of total impurities is as low as 0.3%, as determined by HPLC). In addition, the arformoterol tartrate form D obtained according the fourth aspect of the present invention, contains an amount of the degradation impurity (R)-1-(3-amino-4-hydroxyphenyl)-2-[[(1R)-2-(4-methoxyphenyl)-1-methylethyl]amino]ethanol equal or less than 0.2%, as determined by HPLC. Said arformoterol tartrate form D remains stable and shows no colour variation under temperatures between 5 and 30° C. and atmospheric, vacuum or inert pressures. The inventors of the present invention have also found that arformoterol tartrate form D does not show polymorphic changes when subjected to grinding. Said arformoterol tartrate form D also remains polymorphically and chemically stable and shows no colour variation after at least 6 months of storage under vacuum at 25° C.±2° C. temperature and 60%±5% Relative Humidity (RH), and/or at 40° C.±2° C. temperature and 75%±5% Relative Humidity (RH).

In a similar way as in the fourth aspect, the arformoterol tartrate form D of the present invention can be obtained from other solvates of arformoterol tartrate such as ethyl acetate, acetone, dichloromethane, tetrahydrofuran, methylsulfoxide, dimethylformamide or toluene solvate; preferably ethyl acetate solvate or tetrahydrofuran solvate. Said solvates of arformoterol tartrate can be prepared following the procedure described in the third aspect of the present invention, with the only difference that ethyl acetate or tetrahydrofuran is added in step (c) instead of acetonitrile.

A fifth aspect of the present invention relates to a process for preparing the arformoterol tartrate form D of the first aspect from other polymorphic forms of arformoterol tartrate or mixtures thereof, the process comprising the steps of:
a) providing a mixture of arformoterol tartrate and a solvent selected from an alcohol, water and mixtures thereof, at temperature between 60 and 70° C.;
b) cooling the mixture obtained in step (a) to a temperature between 50 and 55° C.;
c) adding acetonitrile to the mixture obtained in step (b) until a suspension is obtained;

d) cooling the suspension obtained in step (c) while stirring to a temperature between 10 and 30° C. to obtain a solid; and e) collecting the crystals obtained in step (d), and drying the crystals under vacuum at a pressure between 0.75 and 40 mm Hg and at a temperature between 50 and 90° C., to yield arformoterol tartrate form D;

wherein when the solvent used in step in step (a) is a mixture of alcohol and water, the ratio of alcohol/water is between 1:1 and 1:9, preferably between 1:1 and 1:5, more preferably between 1:2 and 1:4.

The ratio of alcohol/water between 1:1 and 1:9 leads towards the formation of form D. As the ratio of alcohol to water increases over 1:1 (i.e. the amount of alcohol is greater than the amount of water), mixtures of form D and form A are obtained. In a preferred embodiment, the alcohol used in step (a) is selected from methanol, ethanol and isopropanol. In a more preferred embodiment, the alcohol is methanol or ethanol.

In one embodiment of the fifth aspect, the arformoterol tartrate provided in step (a) can comprise other polymorphic forms (i.e. other than form D) of arformoterol tartrate and mixtures thereof.

In another preferred embodiment of the fifth aspect, the temperature of the mixture of step (a) is between 60 and 65° C.

In a preferred embodiment of the fifth aspect, the ratio of solvent used in step (a) to the acetonitrile used in step (c) is at least 1:1, preferably between 1:1 and 1:5, more preferably between 1:2 and 1:4. The ratio of solvent in step (a) to acetonitrile of step (c) is not critical, although it is preferred that the amount of acetonitrile is greater than the amount of solvent, since it allows obtaining arformoterol tartrate form D having better yields.

In another preferred embodiment of the fifth aspect, the mixture of step (b) is seeded with arformoterol tartrate form D once the acetonitrile of step (c) is added.

In a preferred embodiment of the fifth aspect, the steps (a) to (d) are performed under inert atmosphere, such as under nitrogen or argon atmosphere. Preferably, they are performed under nitrogen atmosphere.

In a particular embodiment of the fifth aspect, the crystals obtained in step (d) may be further purified, prior to the drying of step (e). In a preferred embodiment, the purification is carried out by crystallization from a single solvent or a combination of solvents, selected from methanol, ethanol and isopropanol; preferably methanol and/or ethanol; more preferably methanol. The crystallization can be carried out more than once, if necessary. Said crystallization may be preferably performed under inert atmosphere, such as under nitrogen or argon atmosphere.

In a particular embodiment, the drying of step (e) is carried out at a pressure that ranges between 0.75 and 40 mm Hg, preferably between 0.75 and 20 mm Hg, more preferably between 0.75 and 3 mm Hg, most preferably between 1.5 and 2.25 mm Hg; and at a controlled temperature between 50 and 90° C., preferably between 60 and 80° C., more preferably at 80° C.

In a more preferred embodiment of the fifth aspect of the present invention, the process for preparing the acetonitrile solvate of arformoterol tartrate of the second aspect from other polymorphic forms of arformoterol tartrate or mixtures thereof comprises the steps of:

a) providing a mixture of arformoterol tartrate and an alcohol at a temperature between 60 and 70° C.;

b) cooling the mixture obtained in step (a) to a temperature between 50 and 55° C.;

c) adding acetonitrile to the mixture obtained in step (b) until a suspension is obtained;

d) cooling the suspension obtained in step (c) while stirring to a temperature between 10 and 30° C. to obtain a solid; and e) collecting the crystals obtained in step (d), and drying the crystals under vacuum at a pressure between 0.75 and 40 mm Hg and at a temperature between 50 and 90° C., to yield arformoterol tartrate form D;

wherein the alcohol used in step (a) is selected from methanol, ethanol and isopropanol, preferably methanol or ethanol.

The method according to the fifth aspect of the present invention is simple, and permits the end product (arformoterol tartrate form D) to be obtained in a high chemical purity (the level of total impurities is as low as 0.3%, as determined by HPLC). In addition, the arformoterol tartrate form D obtained according the fifth aspect of the present invention, contains an amount of the degradation impurity (R)-1-(3-amino-4-hydroxyphenyl)-2-[[(1R)-2-(4-methoxyphenyl)-1-methylethyl]amino]ethanol equal or less than 0.2%, as determined by HPLC. Said arformoterol tartrate form D remains stable and shows no colour variation at ambient conditions, under temperatures between 5 and 30° C. and atmospheric, vacuum or inert pressures. The inventors of the present invention have also found that arformoterol tartrate form D does not show polymorphic changes when grinded. Said arformoterol tartrate form D also remains polymorphically and chemically stable and shows no colour variation after at least 6 months of storage under vacuum at 25° C.±2° C. temperature and 60%±5% Relative Humidity (RH), and/or at 40° C.±2° C. temperature and 75%±5% Relative Humidity (RH).

A sixth aspect of the present invention relates to a process for preparing the arformoterol tartrate form D of the first aspect from arformoterol base, the process comprising the steps of:

a) providing a mixture of arformoterol base with an alcohol, or with a combination of acetonitrile and an alcohol, at a temperature between 15 and 60° C.;

b) adding a solution of L-tartaric acid in a solvent selected from an alcohol, water and mixtures thereof, to the mixture obtained in step (a);

c) cooling the mixture of step (b), when necessary, to a temperature between 30 and 15° C. followed by stirring to obtain a solid;

d) further cooling the mixture of step (c) to a temperature between 0 and 10° C.; and e) collecting the crystals obtained in step (d), and drying the crystals under inlet air pressure and at a temperature between 30 and 50° C. to yield arformoterol tartrate form D.

In a preferred embodiment, the alcohol used in steps (a) and (b) is the same and is selected from methanol, ethanol and isopropanol. In a more preferred embodiment, the alcohol is methanol or ethanol. In the most preferred embodiment, the alcohol is methanol.

In another preferred embodiment of the sixth aspect, the mixture provided in step (a) is a mixture of arformoterol base with an alcohol and the solution used in step (b) is a solution of L-tartaric acid in an alcohol. In a more preferred embodiment, said alcohol used in steps (a) and (b) is the same and is selected from methanol, ethanol and isopropanol, preferably form methanol or ethanol, more preferably is methanol. The use of alcohol in steps (a) and (b) allows obtaining arformoterol tartrate form D having good yield and HPLC purity without the need to use acetonitrile.

The ratio of alcohol/acetonitrile used in step (a), when a combination of an alcohol and acetonitrile is used, is preferably between 1:0.1 and 1:5, more preferably between 1:1 and 1:4.

In another preferred embodiment, the mixture of step (a) is preferably at a temperature between 20 and 60° C.

In another preferred embodiment of the sixth aspect, the mixture of step (b) is seeded with arformoterol tartrate form D once the acetonitrile of step (c) is added.

In another preferred embodiment of the sixth aspect, the temperature of the cooling carried out in step (d) is preferably between 0 and 5° C.

In a preferred embodiment of the sixth aspect, the steps (a) to (d) are performed under inert atmosphere, such as under nitrogen or argon atmosphere. Preferably, they are performed under nitrogen atmosphere.

In a particular embodiment of the sixth aspect, the crystals obtained in step (d) may be further purified, previous to the drying of step (e). In a preferred embodiment, the purification is carried out by crystallization from a single solvent or a combination of solvents, selected from methanol, ethanol and isopropanol; preferably methanol and/or ethanol; more preferably methanol. The crystallization can be carried out more than once, if necessary. Said crystallization may be preferably performed under inert atmosphere, such as under nitrogen or argon atmosphere.

In a preferred embodiment of the sixth aspect, the drying of step (e) is carried out under inlet air pressure (atmospheric pressure); and at a controlled temperature between 30 and 50° C., preferably between 35 and 45° C., more preferably at 40° C. In another embodiment, the drying of step (e) is performed at a pressure between 0.75 and 40 mm Hg, without the use of inlet air pressure; and at a controlled temperature between 30 and 50° C., preferably between 35 and 45° C., more preferably at 40° C.

In a more preferred embodiment of the sixth aspect of the present invention, the process for preparing the arformoterol tartrate form D of the first aspect from arformoterol base comprises the steps of:
  a) providing a mixture of arformoterol base with an alcohol, at a temperature between 15 and 60° C.;
  b) adding a solution of L-tartaric acid in an alcohol, to the mixture obtained in step (a);
  c) cooling the mixture of step (b) to a temperature between 30 and 15° C., when necessary, followed by stirring to obtain a solid;
  d) further cooling the mixture of step (c) to a temperature between 0 and 10° C.; and
  e) collecting the crystals obtained in step (d), and drying the crystals under inlet air pressure and at a temperature between 30 and 50° C. to yield arformoterol tartrate form D;
wherein the alcohol used in step (a) and (b) is selected from methanol, ethanol, or isopropanol, preferably methanol or ethanol, more preferably methanol.

In a more preferred embodiment of the sixth aspect of the present invention, the process for preparing the arformoterol tartrate form D of the first aspect from arformoterol base comprises the steps of:
  a) providing a mixture of arformoterol base with an alcohol, at a temperature between 15 and 60° C.;
  b) adding a solution of L-tartaric acid in an alcohol, to the mixture obtained in step (a);
  c) cooling the mixture of step (b), when necessary, to a temperature between 30 and 15° C. followed by stirring to obtain a solid;
  d) further cooling the mixture of step (c) to a temperature between 0 and 5° C.; and
  e) collecting the crystals obtained in step (d), and drying the crystals under inlet air pressure and at a temperature between 30 and 50° C. to yield arformoterol tartrate form D;
wherein the alcohol used in step (a) and (b) is selected from methanol, ethanol, or isopropanol, preferably methanol or ethanol, more preferably methanol; and the steps (a) to (d) are performed under inert atmosphere, such as under nitrogen or argon atmosphere.

The method according to the sixth aspect of the present invention is simple, and permits the end product (arformoterol tartrate form D) to be obtained in a high chemical purity (the level of total impurities is as low as 0.3%). In addition, the arformoterol tartrate form D obtained according the sixth aspect of the present invention, contains an amount of the degradation impurity (R)-1-(3-amino-4-hydroxyphenyl)-2-[[(1R)-2-(4-methoxyphenyl)-1-methylethyl]amino]ethanol equal or less than 0.2%, as determined by HPLC. Said arformoterol tartrate form D remains stable and shows no colour variation under temperatures between 5 and 30° C. and atmospheric, vacuum or inert pressures. The inventors of the present invention have also found that arformoterol tartrate form D does not show polymorphic changes when grinded. Said arformoterol tartrate form D also remains polymorphically and chemically stable and shows no colour variation after at least 6 months of storage under vacuum at 25° C.±2° C. temperature and 60%±5% Relative Humidity (RH), and/or at 40° C.±2° C. temperature and 75%±5% Relative Humidity (RH).

The crystalline solid arformoterol tartrate obtained or obtainable according to any of the processes described in the fourth, fifth or sixth aspect is a highly pure arformoterol tartrate characterised in that it contains less than 0.5% of total chemical impurities, based on the total weight of the crystalline solid. Additionally, the crystalline solid arformoterol tartrate obtained or obtainable according to any of the processes described in the fourth, fifth or sixth aspect is a highly pure arformoterol tartrate characterised in that it contains less than equal or less than 0.2% of the degradation impurity (R)-1-(3-amino-4-hydroxyphenyl)-2-[[(1R)-2-(4-methoxyphenyl)-1-methylethyl]amino]ethanol) based on the total weight of the crystalline solid. Said crystalline arformoterol tartrate Form D is also characterized by having high polymorphic and chemical stability over time, remaining at least 95%, preferably more than 97%, more preferably more than 99%, in the polymorph Form D; and keeping the levels of total chemical impurities lower than 0.5% (containing an amount of the degradation impurity (R)-1-(3-amino-4-hydroxyphenyl)-2-[[(1R)-2-(4-methoxyphenyl)-1-methylethyl]amino]ethanol equal or less than 0.2%), after at least 6 months of storage under vacuum at 25° C.±2° C. temperature and 60%±5% Relative Humidity (RH), and/or at 40° C.±2° C. temperature and 75%±5% Relative Humidity (RH).

A seventh aspect of the present invention relates to the use of the acetonitrile solvate of the second aspect, in the preparation of arformoterol tartrate form D of the first aspect.

An eighth aspect of the present invention relates to a mixture of form D and polymorph A of arformoterol tartrate.

In a preferred embodiment of the eighth aspect, the mixtures of the invention comprise polymorph A and form D in quantities such that the percentage by weight of form D is at least 30% (w/w), preferably from 40% to 90% (w/w), more preferably form 50% to 80% (w/w), relative to the total weight of form D and polymorph A.

In one embodiment of the eighth aspect, said mixtures of the arformoterol tartrate form D and the known polymorph A of arformoterol tartrate is characterised by a DSC thermogram showing a first endothermic peak with an onset at approximately 123-125° C. and a maximum at approximately 130-131° C.; followed by an exothermic peak with a maximum of approximately 137-138° C.; and a second endothermic peak with a maximum at approximately 191-192° C., a characteristic from known polymorph A.

Figure 3:
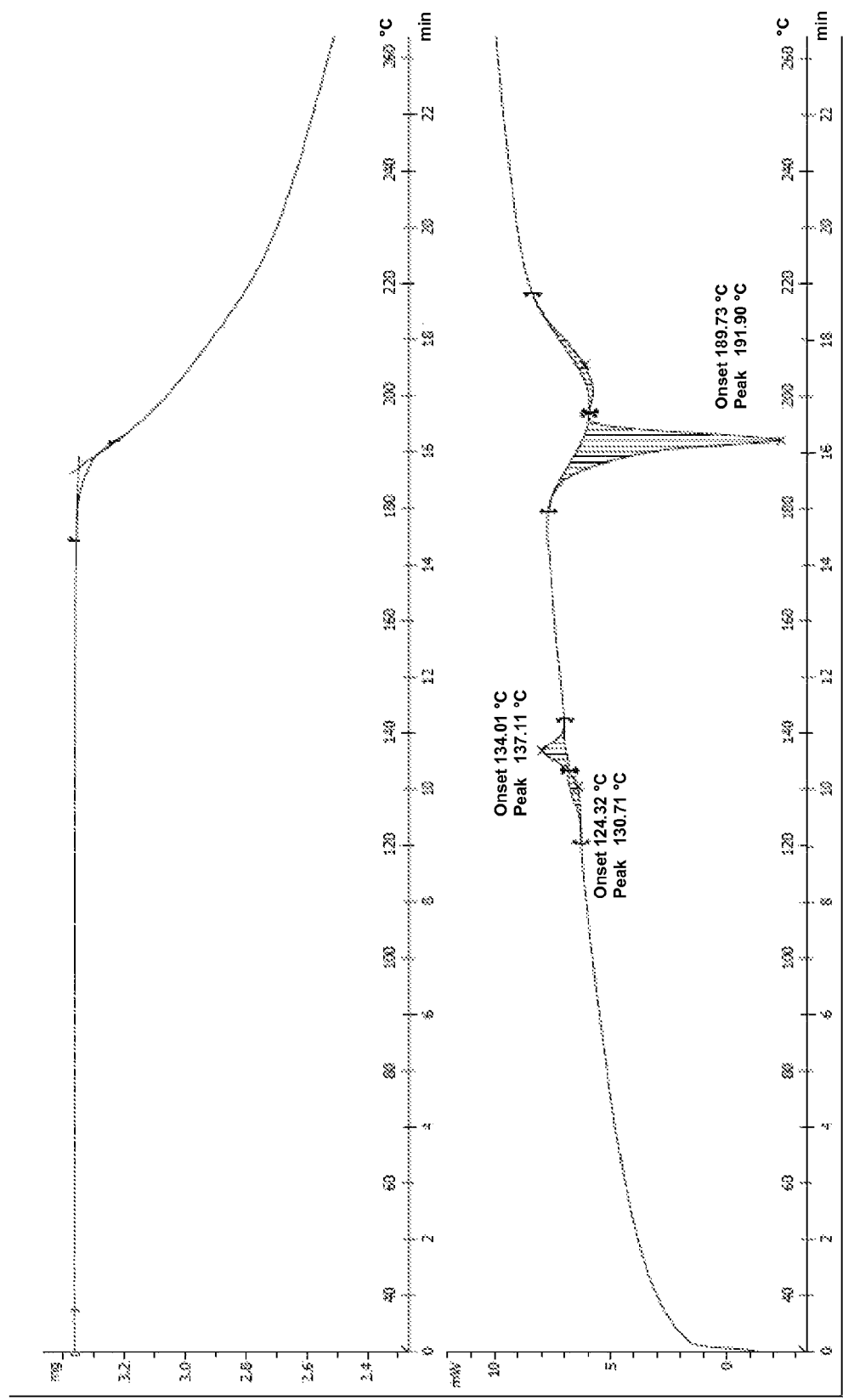
FIG. 3 shows the differential scanning calorimetry (DSC) and the thermogravimetric analysis (TGA) results of arformoterol tartrate form D, in a mixture containing between 40 and 50% of the known polymorph A.

In one example of the eighth aspect, the differential scanning calorimetry (DSC) and the thermogravimetric analysis (TGA) results of the mixtures of arformoterol tartrate form D having between 40 and 50% of the known polymorph A can be depicted substantially as in FIG. 3.

The physical properties of the two separate polymorphs (form D and form A) were compared to the physical properties of mixtures of the invention. It was discovered that polymorphic mixtures with different polymorphic compositions have practically invariable physical properties, in particular thermal characteristics, as compared to the separate polymorphs (form A and form D). Hence, even if there is polymorphic transformation, the thermal characteristics of the polymorphic mixture may remain substantially the same, which is ideal for formulation.

A ninth aspect of the present invention relates to a process for the preparation of mixtures of form D and polymorph A of arformoterol tartrate of the eighth aspect, comprising the steps of:
  a) providing a mixture of arformoterol tartrate and a solvent which is a mixture of an alcohol and water, at a temperature between 60 and 70° C.;
  b) cooling the mixture obtained in step (a) to a temperature between 50 and 55° C.;
  c) adding acetonitrile to the mixture obtained in step (b) until a suspension is obtained;
  d) cooling the suspension obtained in step (c) while stirring to a temperature between 10 and 30° C. to obtain a solid; and
  e) collecting the crystals obtained in step (d) and drying the crystals under vacuum at a pressure between 0.75 and 40 mm Hg and at a temperature between 50 and 90° C.;
wherein the ratio of alcohol:water used in step (a) is over 1:1 and up to 5:1, preferably between 2:1 and 4:1, more preferably 3:1 and 4:1. As previously described for the third aspect, the ratio of alcohol/water between 1:1 and 1:9 leads to the formation of form D instead of form A. As the ratio of alcohol to water increases over 1:1, mixtures of form D and form A are obtained. In a preferred embodiment, the alcohol used in step (a) is selected from methanol and ethanol.

In one embodiment of the ninth aspect, the arformoterol tartrate of step (a) can be crystallised from other polymorphic forms of arformoterol tartrate (i.e. other than form D) and mixtures thereof.

In another preferred embodiment of the ninth aspect, the temperature of the mixture of step (a) is between 60 and 65° C.

In a preferred embodiment of the ninth aspect, the ratio of solvent used in step (a) to the acetonitrile used in step (c) is at least 1:1, preferably between 1:1 and 1:5, more preferably between 1:1 and 1:4, most preferably between 1:2 and 1:3. The ratio of solvent in step (a) to acetonitrile of step (c) is not critical, although it is preferred that, when used, the amount of acetonitrile is greater than the amount of solvent, since it allows obtaining mixtures of form D and polymorph A of arformoterol tartrate having good yields.

In a preferred embodiment of the ninth aspect, the steps (a) to (d) are performed under inert atmosphere, such as under nitrogen or argon atmosphere. Preferably, they are performed under nitrogen atmosphere.

In a particular embodiment of the ninth aspect, the crystals obtained in step (d) may be further purified, previous to the drying of step (e). In a preferred embodiment, the purification is carried out by crystallization from a single solvent or combination of solvents, selected from methanol, ethanol and isopropanol; preferably methanol and/or ethanol; more preferably methanol. The crystallization can be carried out more than once, if necessary. Said crystallization may be preferably performed under inert atmosphere, such as under nitrogen or argon atmosphere.

In a particular embodiment, the drying of step (e) is carried out at a pressure that ranges between 0.75 and 40 mm Hg, preferably between 0.75 and 20 mm Hg, more preferably between 0.75 and 3 mm Hg; and at a controlled temperature between 50 and 90° C., preferably between 60 and 80° C.

The method according to the ninth aspect of the present invention is simple, and permits to obtain mixtures of the form D and the known polymorph A of arformoterol tartrate in a high chemical purity (the level of total impurities is as low as 0.3%, as determined by HPLC).

The arformoterol tartrate obtained or obtainable according to any of the processes described in the fourth, fifth, sixth or ninth aspect has a particle size distribution $d_{50}$ equal to or less than 100 μm, preferably less than 50 μm, more preferably less than 20 μm, still more preferably less than 10 μm and most preferably less than 5 μm.

A tenth aspect of the present invention relates to a pharmaceutical composition comprising arformoterol tartrate form D, or a mixture of form D and polymorph A of arformoterol tartrate, and at least one pharmaceutically acceptable excipient. The composition may be in liquid form (e.g. a solution or suspension), or a solid form (e.g. powder for inhalation).

In compositions according to the tenth aspect and containing a mixture of form D and polymorph A of arformoterol tartrate, the composition may be such that the percentage by weight of form D is at least 30% (w/w), preferably from 40% to 90% (w/w), more preferably form 50% to 80% (w/w) relative to the total weight of form D and polymorph A.

An eleventh aspect of the invention relates to arformoterol tartrate form D, a mixture according to the eighth aspect, or a pharmaceutical composition according to the tenth aspect, for use in therapy.

A twelfth aspect relates to form D, a mixture according to the eighth aspect, or a pharmaceutical composition according to the tenth aspect, for use as a bronchodilator.

A thirteenth aspect of the invention relates to a method of effecting bronchodilation in a subject in need thereof, the method comprising administering to the subject a therapeutically effective amount of arformoterol tartrate form D, or a mixture of form D and polymorph A of arformoterol tartrate, or a pharmaceutical composition according to the tenth aspect.

Pharmaceutical compositions of the present invention can be in liquid form or in solid form. Arformoterol is commercialized as a solution for inhalation packaged in 2.1 mL unit-dose, low-density polyethylene (LDPE) unit-dose vials. Each unit-dose vial contains 15 mcg of arformoterol (equivalent to 22 mcg of arformoterol tartrate) in a sterile, isotonic saline solution, and additional excipients of a standard nature for such compositions.

Solid pharmaceutical compositions may typically be appropriate when combining arformoterol tartrate with other active ingredients, such as an inhaled corticosteroid, such as ciclesonide. Form D of arformoterol tartrate or form D/polymorph A mixtures (as described above) are also useful for the preparation of such solid pharmaceutical compositions.

It is to be understood that, where preferred features are presented above in relation to a particular aspect of the invention, those features may also be preferred in other aspects of the invention, as appropriate.

Further aspects/embodiments of the present invention can be found in the following clauses:

1. A polymorphic form of arformoterol tartrate, designated as form D, which is characterised by at least one of the following:
(i) a powder X-ray diffraction pattern having peaks at approximately 6.8, 13.3, 13.6, 13.8, 14.1, 18.2, 18.7, 20.0±0.2 degrees two theta; or
(ii) a DSC thermogram showing an endothermic peak with an onset at approximately 119-120° C., and a maximum at approximately 129-131° C., followed by an exothermic peak with a maximum at approximately 137-138° C.;
wherein the DSC thermogram of form D has a further endothermic peak with an onset at approximately 168-170° C.

2. The polymorph of arformoterol tartrate according to clause 1, wherein the powder X-ray diffraction pattern comprises interplanar distance values at approximately 13.01, 6.65, 6.49, 6.40, 6.27, 4.87, 4.73 and 4.44 Å.

3. The polymorph of arformoterol tartrate according to any of the preceding clauses, wherein the powder X-ray diffraction pattern further comprises one or more additional peaks at about 7.4, 15.9, 25.1 and 25.8±0.2 degrees two theta.

4. The polymorph of arformoterol tartrate according to any of the preceding clauses, wherein the powder X-ray diffraction pattern further comprises one or more interplanar distance values at approximately 11.99, 5.58, 3.54 and 3.45 Å.

5. The polymorph of arformoterol tartrate according to any of the preceding clauses, having a powder X-ray diffraction pattern in accordance with FIG. 1.

6. The polymorph of arformoterol tartrate according to any of the preceding clauses, showing no weight loss before decomposition which is observed at temperatures over 167° C.

7. The polymorph of arformoterol tartrate according to any of the preceding clauses characterised in that it contains less than 0.5% of total chemical impurities based on the total weight of the compound.

8. The polymorph of arformoterol tartrate according to any of the preceding clauses, characterised in that it contains equal or less than 0.2% of the degradation impurity (R)-1-(3-amino-4-hydroxyphenyl)-2-[[(1R)-2-(4-methoxyphenyl)-1-methylethyl]amino]ethanol) based on the total weight of the compound.

9. An acetonitrile solvate of arformoterol tartrate characterised by at least one of the following:
(i) a powder X-ray diffraction pattern showing the following peaks at approximately 6.5, 13.7, 17.9, 18.4, 20.3, 21.6, 24.6 and 24.8±0.2 degrees two theta; or
(ii) a DSC thermogram showing an endothermic peak with an onset at approximately 124-125° C., and a maximum at approximately 134-136° C., followed by an exothermic peak with a maximum at approximately 140-141° C.;
wherein the DSC thermogram of form D has a further endothermic peak with an onset at approximately 170-172° C.

10. The acetonitrile solvate of arformoterol tartrate according to clause 9, wherein the powder X-ray diffraction pattern comprises interplanar distance values at approximately 13.66, 6.46, 4.95, 4.81, 4.37, 4.10, 3.62 and 3.59 Å.

11. The acetonitrile solvate of arformoterol tartrate according to any of the clauses 9 to 10, wherein the powder X-ray diffraction pattern further comprises one or more additional peaks at about 13.2, 16.6, 19.2, 23.3, and 25.1±0.2 degrees two theta.

12. The acetonitrile solvate of arformoterol tartrate according to any of clauses 9 to 11, wherein the powder X-ray diffraction pattern further comprises one or more interplanar distance values at approximately 6.72, 5.32, 4.62, 3.82 and 3.54 Å.

13. The acetonitrile solvate of arformoterol tartrate according to any of clauses 9 to 12, having a powder X-ray diffraction pattern in accordance with FIG. 2.

14. The acetonitrile solvate of arformoterol tartrate according to any of clauses 9 to 13, which contains an amount of acetonitrile in a range between 0.2 and 5% (w/w), preferably in an amount between 1.6 and 4.1% (w/w), more preferably in an amount between 2 and 4% (w/w).

15. Use of the acetonitrile solvate of arformoterol according to any of clauses 9 to 14, as an intermediate in the preparation of the form D of arformoterol tartrate of clauses 1 to 6.

16. A process for preparing acetonitrile solvate of arformoterol tartrate, as defined in any of the clauses 9 to 14, from other polymorphic forms of arformoterol tartrate comprising the steps of:
a) providing a mixture of arformoterol tartrate and a solvent selected from and alcohol, water and mixtures thereof, at temperature between 60 and 70° C.;
b) cooling the mixture obtained in step (a) to a temperature between 50 and 55° C.;
c) adding acetonitrile to the mixture obtained in step (b) until a suspension is obtained;
d) cooling the suspension obtained in step (c) while stirring to a temperature between 10 and 30° C. to obtain a solid; and
e) collecting the crystals obtained in step (d) and drying the crystals under vacuum at a pressure between at a pressure between 0.75 and 40 mm Hg; and at a temperature between 20 and 45° C. to yield acetonitrile solvate of arformoterol tartrate;
wherein when the solvent used in step in step (a) is a mixture of alcohol and water, the ratio of alcohol:water is between 1:1 and 1:9.

17. The process according to clause 16, wherein the alcohol used in step (a) is preferably selected from methanol, ethanol and isopropanol.

18. The process according to the preceding clause, wherein the preferred alcohol used in step (a) is methanol or ethanol.

19. The process according to any of the clauses 16 to 18 wherein the solvent of step (a) is a mixture of alcohol/water in a ratio between 1:1 and 1:5.

20. The process according to the preceding clause, wherein the ratio of the mixture of alcohol/water is preferably between 1:1 and 1:4.

21. The process according to any of clauses 16 to 20, wherein the temperature of the mixture of step (a) is preferably between 60 and 65° C.

22. The process according to any of the clauses 16 to 21, wherein the ratio of the solvent used in step (a) and the acetonitrile used in step (c) is of at least 1:1, preferably between 1:1 and 1:5.

23. The process according to the preceding clause, wherein the ratio the solvent used in step (a) and the acetonitrile used in step (c) is preferably between 1:2 and 1:4.

24. The process according to any of the clauses 16 to 23, wherein the drying carried out in step (e) is performed at a pressure between 0.75 and 40 mm Hg, preferably between 0.75 and 20 mm Hg, more preferably between 0.75 and 3 mm Hg, most preferably between 1.5 and 2.25 mm Hg.

25. The process according to any of the clauses 16 to 24, wherein the drying carried out in step (e) is preferably performed at a temperature between 25 and 40° C., more preferably between 30 and 40° C.

26. A process for preparing arformoterol tartrate form D, as defined in any of the clauses 1 to 6, comprising the step of drying crystals of acetonitrile solvate of arformoterol tartrate, as defined in any of the clauses 9 to 14, under vacuum at a pressure between 0.75 and 40 mm Hg; and at a temperature between 50 and 90° C.

27. The process according to the clause 26, wherein the drying is preferably performed at a pressure between 0.75 and 20 mm Hg, more preferably between 0.75 and 3 mm Hg, most preferably between 1.5 and 2.25 mm Hg.

28. The process according to any of the two preceding clauses, wherein the drying is preferably performed at a temperature between 60 and 80° C., more preferably at 80° C.

29. A process for preparing arformoterol tartrate form D, as defined in any of the clauses 1 to 8, from other polymorphic forms of arformoterol tartrate, comprising the steps of:
   a) providing a mixture of arformoterol tartrate and a solvent selected from an alcohol, water and mixtures thereof, at temperature between 60 and 70° C.;
   b) cooling the mixture obtained in step (a) to a temperature between 50 and 55° C.;
   c) adding acetonitrile to the mixture obtained in step (b) until a suspension is obtained;
   d) cooling the suspension obtained in step (c) while stirring to a temperature between 10 and 30° C. to obtain a solid; and
   e) collecting the crystals obtained in step (d) and drying the crystals under vacuum at a pressure between 0.75 and 40 mm Hg and at a temperature between 50 and 90° C. to yield arformoterol tartrate form D;
   wherein when the solvent used in step in step (a) is a mixture of alcohol and water, the ratio of alcohol:water is between 1:1 and 1:9.

30. The process according to clause 29, wherein the alcohol used in step (a) is preferably selected from methanol, ethanol and isopropanol.

31. The process according to the preceding clause, wherein the preferred alcohol used in step (a) is methanol or ethanol.

32. The process according to any of the clauses 29 to 31, wherein the solvent of step (a) is a mixture of alcohol/water in a ratio between 1:1 and 1:5.

33. The process according to the preceding clause, wherein the ratio of the mixture of alcohol/water is preferably between 1:1 and 1:4.

34. The process according to clauses 29 to 33, wherein the temperature of the mixture of step (a) is preferably between 60 and 65° C.

35. The process according to any of the clauses 29 to 34, wherein the ratio of the solvent used in step (a) and the acetonitrile used in step (c) is at least 1:1, preferably between 1:1 and 1:5.

36. The process according to the preceding clause, wherein the ratio the solvent used in step (a) and the acetonitrile used in step (c) is preferably between 1:2 and 1:4.

37. The process according to any of the clauses 29 to 36, wherein the drying carried out in step (e) is preferably performed at a pressure between 0.75 and 20 mm Hg, more preferably between 0.75 and 3 mm Hg, most preferably between 1.5 and 2.25 mm Hg.

38. The process according to the any of the clauses 29 to 37, wherein the drying is preferably performed at a pressure between 0.75 and 20 mm Hg, more preferably between 0.75 and 3 mm Hg, most preferably between 1.5 and 2.25 mm Hg.

39. The process according to any of the clauses 29 to 38, wherein the drying carried out in step (e) is preferably performed at a temperature between 60 and 80° C., more preferably at 80° C.

40. A process for preparing arformoterol tartrate form D, as defined in any of the clauses 1 to 8, from arformoterol base, comprising the steps of:
   a) providing a mixture of arformoterol base with an alcohol or with a combination of acetonitrile and an alcohol at a temperature between 15 and 60° C.;
   b) adding a solution of L-tartaric acid in a solvent selected from an alcohol, water and mixtures thereof, to the mixture obtained in step (a);
   c) cooling the mixture of step (b) to a temperature between 30 and 15° C., when necessary, followed by stirring to obtain a solid;
   d) further cooling the mixture of step (c) to a temperature between 0 and 10° C.; and
   e) collecting the crystals obtained in step (d) and drying the crystals under inlet air pressure and at a temperature between 30 and 50° C. to yield arformoterol tartrate form D;

41. The process according to the clause 40, wherein the mixture provided in step (a) is a mixture of arformoterol base with an alcohol, selected from methanol, ethanol, or isopropanol; preferably methanol or ethanol; more preferably methanol.

42. The process according to the clause 40, wherein the solution used in step (b) is a solution of L-tartaric acid in an alcohol, selected from methanol, ethanol, or isopropanol; preferably methanol or ethanol; more preferably methanol.

43. The process according to the clause 40, wherein the alcohol used in steps (a) and (b) is the same.

44. The process according to any of the clauses 40 to 43, wherein the alcohol of steps (a) and (b) is selected from methanol, ethanol and isopropanol.

45. The process according to the preceding clause, wherein the preferred alcohol used in step (a) and/or step (b) is methanol or ethanol.

46. The process according to the preceding clause, wherein the most preferred alcohol used in step (a) and/or step (b) methanol 47. The process according to any of the clause 40 to 46, wherein the ratio of the alcohol/acetonitrile used in step (a) is of at least 1:0.1, preferably between 1:1 and 1:5

48. The process according to the preceding clause, wherein the ratio of the alcohol/acetonitrile is preferably between 1:1 and 1:4.

49. The process according to any of clauses 40 to 48, wherein the mixture of step (a) is preferably at a temperature between 20 and 60° C.

50. The process according to any of the clauses 40 to 49, wherein the temperature of the cooling carried out in step (d) is preferably between 0 and 5° C.

51. The process according to any of the clauses 40 to 50, wherein the steps (a) to (d) are performed under inert atmosphere, such as under nitrogen or argon atmosphere; preferably, under nitrogen atmosphere.

52. The process according to the any of the clauses 40 to 51, wherein the drying carried out in step (e) is performed at a pressure of 760 mm Hg.

53. The process according to the any of the clauses 40 to 52, wherein the drying carried out in step (e) is performed at a pressure between 0.75 and 40 mm Hg, without the use of inlet air pressure.

54. The process according to any of the clauses 40 to 53, wherein the temperature of the drying carried out in step (e) is preferably between 35 and 45° C., more preferably at 40° C.

55. The arformoterol tartrate form D, as defined in any of the clauses 1 to 8, having at least 30% (w/w) of form D, preferably from 40% to 90% (w/w), more preferably form 50% to 80% (w/w) relative to the total weight of form D and polymorph A.

56. The arformoterol tartrate form D of clause 55, having between 40 and 50% of the known polymorph A.

57. The arformoterol tartrate form D of any of the two preceding clauses characterised by a DSC thermogram showing a first endothermic peak with an onset at approximately 124-125° C. and a maximum at approximately 130-131° C.; followed by an exothermic peak with a maximum of approximately 137-138° C., and a second endothermic peak with a maximum at approximately 191-192° C.

58. The arformoterol tartrate form D of any of the three preceding clauses, having a differential scanning calorimetry (DSC) and a thermogravimetric analysis (TGA) thermograms in accordance with FIG. 3.

59. A process for preparing the arformoterol tartrate form D of any of the three preceding clauses, from other polymorphic forms of arformoterol tartrate, comprising the steps of:
   a) providing a mixture of arformoterol tartrate and a solvent selected from an alcohol, water and mixtures thereof, at temperature between 60 and 70° C.;
   b) cooling the mixture obtained in step (a) to a temperature between 50 and 55° C.;
   c) adding acetonitrile to the mixture obtained in step (b) until a suspension is obtained;
   d) cooling the suspension obtained in step (c) while stirring to a temperature between 10 and 30° C. to obtain a solid; and
   e) collecting the crystals obtained in step (d) and drying the crystals under vacuum at a pressure 0.75 and 40 mm Hg and at a temperature between 50 and 90° C.;
   wherein the ratio of alcohol:water used in step (a) is over 1:1 and up to 5:1

60. The process according to clause 59, wherein the alcohol used in step (a) is preferably selected from methanol and ethanol.

61. The process according to the preceding clause, wherein the preferred alcohol used in step (a) is ethanol.

62. The process according to clauses 59 to 61, wherein the ratio of the mixture of alcohol/water of step (a) is preferably between 3:1 and 4:1, more preferably 4:1.

63. The process according to any of clauses 59 to 62, wherein the temperature of the mixture of step (a) is preferably between 60 and 65° C.

64. The process according to any of the clauses 59 to 63, wherein the ratio of the solvent used in step (a) and the acetonitrile used in step (c) is at least 1:1, preferably between 1:1 and 1:4.

65. The process according to the preceding clause, wherein the ratio the solvent used in step (a) and the acetonitrile used in step (c) is preferably between 1:2 and 1:3.

66. The process according to any of the clauses 59 to 65, wherein the drying carried out in step (e) is preferably performed at a pressure between 0.75 and 20 mm Hg, more preferably between 0.75 and 3 mm Hg, most preferably between 1.5 and 2.25 mm Hg.

67. The process according to any of the clauses 59 to 66, wherein the drying carried out in step (e) is preferably performed at a temperature between 60 and 80° C.

68. The arformoterol tartrate, as defined in any of the clauses 1 to 8 or 55 to 58, obtained or obtainable according to the process described in any of the clauses 26 to 54 or 59 to 67.

69. Pharmaceutical composition comprising a therapeutically effective amount of the arformoterol tartrate obtained according to any of clauses 26 to 67 and at least one pharmaceutically acceptable excipient or carrier.

70. Pharmaceutical composition containing arformoterol tartrate obtained by mixing form D of arformoterol tartrate according to any of clauses 1 to 8, and at least one pharmaceutically acceptable excipient, and its use as a bronchodilator.

71. Pharmaceutical composition of arformoterol tartrate obtained by mixing form D according to any of clauses 1-8 and polymorph A in a weight to weight ratio such that form D is present in an amount of at least 30% (w/w), preferably from 40% to 90% (w/w), more preferably form 50% to 80% (w/w) relative to the total weight of form D and polymorph A, and at least one pharmaceutically acceptable excipient, and its use as a bronchodilator.

72. A pharmaceutical composition comprising a therapeutically effective amount of the arformoterol tartrate according to any of the clauses 1 to 8, and 55 to 58 and at least one pharmaceutically acceptable excipient or carrier.

73. The arformoterol tartrate form D according to any of clauses 1-8, for use as a bronchodilator.

74. The arformoterol tartrate according to any of clauses 55 to 58, for use as a bronchodilator.

75. The arformoterol tartrate according to any of clauses 1 to 8, or 55 to 58, for use as a medicament.

76. The use of arformoterol tartrate according to any of the clauses 1 to 8, or 55 to 58, as a bronchodilator.

77. A method of effecting bronchodilation, the method comprising the administration, to a subject in need of such treatment, of a therapeutically effective amount of arformoterol tartrate according to any of the clauses 1 to 6, or 53 to 56, or a pharmaceutical composition according to any of the clauses 67 to 70.

The present invention is further illustrated by the following examples. They should in no case be interpreted as a limitation of the scope of the invention as defined in the claims.

EXAMPLES

General Methods

Powder X-Ray Diffraction (PXRD) patterns were acquired on a D8 Advance Series 2Theta/Theta powder diffraction system using $Cu_{K\alpha 1}$-radiation (1.54060 Ångström) in transmission geometry. The system was equipped with a VÅNTEC-1 single photon counting PSD, a Germanium monochromator, a ninety positions auto changer sample stage, fixed divergence slits and radial soller. The samples were prepared and placed in standard sample holders using two foils of polyacetate. One hour scans in a range from 4° to 40° in 2θ were carried out.

Programs used: data collection with DIFFRAC plus XRD Commander V.2.5.1 and evaluation with EVA V.12.0.

Differential Scanning calorimetry (DSC) analysis was recorded in a Mettler Toledo DSC822e calorimeter. Experimental conditions: 40 µL aluminium crucibles; atmosphere of dry nitrogen at 50 mL/min flow rate; heating rate of 10° C./min between 30 and 300° C. Data collection and evaluation was done with software STARe.

Thermogravimetric (TGA) analysis was recorded in a Mettler Toledo SDTA851e thermobalance. Experimental conditions: 40 µL aluminium crucibles; atmosphere of dry nitrogen at 80 mL/min flow rate; heating rate of 10° C./min between 30 and 300° C. Data collection and evaluation was done with software STARe.

Example 1

Synthesis of (R,R)-Formoterol-L-tartrate Form D

A solution containing 3.9 g (26 mmol) of L-tartaric acid and 36 mL of methanol was added to a solution of 9 g (26 mmol) of arformoterol base and 144 mL methanol at 23° C. Afterwards, the resulting mixture was seeded with form D and stirred at 23° C. for 1 hour. It was then further cooled to 0-5° C. for 1 hour and the product collected by filtration and dried under inlet air (atmospheric pressure) for 16 hours to provide 11.1 g (86% yield) (99.7% chemical purity, containing 0.14% of the degradation impurity (R)-1-(3-amino-4-hydroxyphenyl)-2-[[(1R)-2-(4-methoxyphenyl)-1-methylethyl]amino]ethanol) of (R,R)-formoterol L-tartrate form D, as an off white powder. $^1$H-NMR (200 MHz, $d_6$-DMSO) δ: 1.03 (d, 3H); 2.50-2.67 (m, 5H); 3.72 (s, 3H); 3.99 (s, 2H); 4.65-4.85 (m, 1H); 6.82-7.15 (m, 5H); 8.02 (s, 1H); 8.28 (s, 1H); 9.60 (s, NH). No residual solvent was detected ($^1$H-NMR).
PSD: $d_{50}$=2.3 μm.

Example 2

Synthesis of (R,R)-Formoterol-L-tartrate Form D

A solution of 4.2 g (28 mmol) of L-tartaric acid and 36 mL of methanol was added to a solution of 9.7 g (28 mmol) of arformoterol base 41 mL methanol and 117 mL acetonitrile at 23° C. Afterwards, the resulting mixture was seeded with form D and stirred at 23° C. for 1 hour. It was then further cooled to 0-5° C. for 1 hour and the product collected by filtration and dried under inlet air (atmospheric pressure) at 40° C. for 16 hours to provide 12.6 g (91% yield) (99.5% chemical purity) of (R,R)-formoterol L-tartrate form D, as an off white powder. 1H-NMR (200 MHz, d6-DMSO) δ: 1.03 (d, 3H); 2.50-2.67 (m, 5H); 3.72 (s, 3H); 3.99 (s, 2H); 4.65-4.85 (m, 1H); 6.82-7.15 (m, 5H); 8.02 (s, 1H); 8.28 (s, 1H); 9.60 (s, NH). 0.2% residual (i.e. non-solvated) acetonitrile was detected (1H-NMR).

Example 3

Synthesis of (R,R)-Formoterol-L-tartrate Form D

A solution of 4.2 g (28 mmol) of L-tartaric acid and 36 mL of ethanol was added to a solution of 9.7 g (28 mmol) of arformoterol base, 41 mL ethanol and 117 mL acetonitrile at 23° C. Then, the resulting mixture was stirred at 23° C. for 1 hour. It was then further cooled to 0-5° C. for 1 hour and the product collected by filtration. The product was dried under inlet air (atmospheric pressure) at 40° C. for 16 hours to provide 12.4 g (89% yield) (99% chemical purity) of (R,R)-formoterol L-tartrate form D, as an off white powder. $^1$H-NMR (200 MHz, d6-DMSO) δ: 1.03 (d, 3H); 2.50-2.67 (m, 5H); 3.72 (s, 3H); 3.99 (s, 2H); 4.65-4.85 (m, 1H); 6.82-7.15 (m, 5H); 8.02 (s, 1H); 8.28 (s, 1H); 9.60 (s, NH).

Example 4

Synthesis of (R,R)-Formoterol-L-tartrate Form D

A solution of 4.2 g (28 mmol) of L-tartaric acid and 46 ml of ethanol was added to a solution of 9.6 g (28 mmol) of arformoterol base 31 mL ethanol and 117 mL acetonitrile at 60° C. Afterwards, the resulting mixture was cooled at 23° C. and stirred at this temperature for 1 hour. It was then further cooled to 0-5° C. for 1 hour and the product collected by filtration and dried under inlet air (atmospheric pressure) at 40° C. for 16 hours to provide 12.2 g (89% yield) (99.6% chemical purity) of (R,R)-formoterol L-tartrate form D, as an off white powder. 1H-NMR (200 MHz, d6-DMSO) δ: 1.03 (d, 3H); 2.50-2.67 (m, 5H); 3.72 (s, 3H); 3.99 (s, 2H); 4.65-4.85 (m, 1H); 6.82-7.15 (m, 5H); 8.02 (s, 1H); 8.28 (s, 1H); 9.60 (s, NH). No residual solvent was detected (1H-NMR).

Example 5

Synthesis of (R,R)-Formoterol-L-tartrate Form D

A solution of 4.2 g (28 mmol) of L-tartaric acid and 21 mL of water was added to a solution of 9.7 g (28 mmol) of arformoterol base, 70 mL methanol and 105 mL acetonitrile at 23° C. Afterwards, the resulting mixture was seeded with form D and stirred at this temperature for 1 hour. It was then further cooled to 0-5° C. for 1 hour and the product collected by filtration and dried under inlet air (atmospheric pressure) at 40° C. for 16 hours to provide 11.5 g (83% yield) (99.9% chemical purity) of (R,R)-formoterol L-tartrate form D, as an off white powder. 1H-NMR (200 MHz, d6-DMSO) δ: 1.03 (d, 3H); 2.50-2.67 (m, 5H); 3.72 (s, 3H); 3.99 (s, 2H); 4.65-4.85 (m, 1H); 6.82-7.15 (m, 5H); 8.02 (s, 1H); 8.28 (s, 1H); 9.60 (s, NH). 0.2% residual (i.e. non-solvated) acetonitrile was detected (1H-NMR).

Example 6

Synthesis of (R,R)-Formoterol-L-tartrate Form D

A suspension of 9 g (18 mmol) of arformoterol-L-tartrate form B and 270 mL of methanol was heated at 60° C. until solution. Afterwards, to the resulting mixture was added 360 mL of acetonitrile until a suspension was obtained. The suspension was cooled at 23° C. and stirred at this temperature for 1 hour. It was then further cooled to 0-5° C. for 1 hour and the product collected by filtration and dried inlet air (atmospheric pressure) at 40° C. for 16 hours to provide 8.1 g (90% yield) (99.8% chemical purity) of (R,R)-formoterol L-tartrate form D, as an off white powder. $^1$H-NMR (200 MHz, d6-DMSO) δ: 1.03 (d, 3H); 2.50-2.67 (m, 5H); 3.72 (s, 3H); 3.99 (s, 2H); 4.65-4.85 (m, 1H); 6.82-7.15 (m, 5H); 8.02 (s, 1H); 8.28 (s, 1H); 9.60 (s, NH).

Example 7

Synthesis of (R,R)-Formoterol-L-tartrate Form D

A suspension of 1.073 g (2.16 mmol) of (R,R)-arformoterol tartrate Form B in 30 mL of methanol was heated to the reflux temperature of the solvent for 15 minutes until a clear yellow-orange solution was obtained. Afterwards, it was cooled to about 60-50° C. and followed by addition of 10 mL aliquots of acetonitrile (total of 40 mL) at the same temperature until a suspension was obtained. The suspension was further cooled to 10-40° C. and stirred at this temperature for 10 minutes. The product was collected by filtration, washed with acetonitrile and dried under vacuum (2 mbar, equivalent to 1.5 mm Hg) at 80° C. for 15 hours to provide 773 mg (73% yield) of (R,R)-formoterol L-tartrate form D, which contained no solvent detected by 1H-NMR or TGA analysis.

Example 8

Synthesis of Acetonitrile Solvate of (R,R)-Formoterol-L-tartrate

A suspension of 348.8 mg (0.70 mmol) of (R,R)-arformoterol tartrate Form B in 15 mL of methanol was heated to the reflux temperature of the solvent for 15 minutes or until a clear yellow solution was obtained. Afterwards, it was cooled to about 60-50° C. and followed by addition of 5 mL aliquots of acetonitrile (total of 45 mL) at the same temperature until a suspension was obtained. The suspension was further cooled to 10-40° C. and stirred at this temperature for 10 minutes. The product was collected by filtration, washed with acetonitrile and dried under vacuum (2 mbar, equivalent to 1.5 mm Hg) at 40° C. for 12 hours to provide 262.4 mg (75% yield) of acetonitrile solvate of (R,R)-Formoterol-L-tartrate, which contained acetonitrile in a range between 2 and 4% (w/w), as determined by 1H-NMR or TGA analysis.

Example 9

Synthesis of (R,R)-Formoterol-L-tartrate Form D

Acetonitrile solvate of (R,R)-Formoterol-L-tartrate prepared according to example 8, was dried under vacuum (2 mbar, equivalent to 1.5 mm Hg) at 80° C. for 16 hours to obtain (R,R)-Formoterol-L-tartrate form D, which contained no solvent detected by $^1$H-NMR or TGA analysis.

Example 10

Synthesis of Acetonitrile Solvate of (R,R)-Formoterol-L-tartrate

A suspension of 135 mg (0.27 mmol) of (R,R)-arformoterol tartrate Form A and 7.5 mL of methanol was heated to the reflux temperature of the solvent for 10 min. Then, the solution obtained was allowed to cool to about 50-60° C., followed by addition of 19 mL of acetonitrile at the same temperature. Afterwards, the solution was cooled to room temperature and stirred for 1 hour. The product was collected by filtration, washed with acetonitrile and dried under vacuum (2-3 mbar, equivalent to 1.5-2.25 mm Hg) at 25° C. for 1 hour to provide acetonitrile solvate of (R,R)-Formoterol-L-tartrate, which contained about 2.5% (w/w) of acetonitrile, as determined by 1H-NMR analysis.

Example 11

Synthesis of (R,R)-Formoterol-L-tartrate Form D

Acetonitrile solvate of (R,R)-Formoterol-L-tartrate prepared according to example 10 was dried under vacuum (2-3 mbar, equivalent to 1.5-2.25 mm Hg) at 80° C. for 1 hour to obtain (R,R)-Formoterol-L-tartrate form D, which contained no solvent detected by TGA analysis.

Example 13

Synthesis of Acetonitrile Solvate of (R,R)-Formoterol-L-tartrate

A suspension of 407.3 mg (0.82 mmol) of (R,R)-arformoterol tartrate Form B and 15 mL of methanol was heated to the reflux temperature of the solvent for 15 min. Then, the solution obtained was allowed to cool to about 50-60° C., followed by addition of 45 mL of acetonitrile at the same temperature. Afterwards, the solution was cooled to room temperature and stirred for 30 minutes. The product was collected by filtration, washed with acetonitrile and dried under vacuum (2-3 mbar, equivalent to 1.5-2.25 mm Hg) at 60° C. for 2 hours to provide 345.5 mg (85% yield) of acetonitrile solvate of (R,R)-Formoterol-L-tartrate, which contained about 1.6% (w/w) of acetonitrile, as determined by TGA analysis.

Example 14

Synthesis of Acetonitrile Solvate of (R,R)-Formoterol-L-tartrate

A suspension of 1.007 g (2 mmol) of (R,R)-arformoterol tartrate Form A and 65 mL of methanol was heated to the reflux temperature of the solvent for 30 min. Then, the solution obtained was cooled to 50° C. in 30 min, followed by addition of 90 mL of acetonitrile at the same temperature for 10 minutes. Afterwards, the solution was cooled to 30° C. in 30 minutes and stirred at room temperature for 2 hours. The product was collected by filtration, washed with acetonitrile and dried under vacuum (2-3 mbar, equivalent to 1.5-2.25 mm Hg) at 40° C. for 17 hours to provide acetonitrile solvate of (R,R)-Formoterol-L-tartrate, which contained about 2.7% (w/w) of acetonitrile, as determined by TGA analysis.

Example 15

Synthesis of (R,R)-Formoterol-L-tartrate Form D

Acetonitrile solvate of (R,R)-Formoterol-L-tartrate prepared according to example 14 was dried under vacuum (2-3 mbar, equivalent to 1.5-2.25 mm Hg) at 60° C. for 2 hours to obtain (R,R)-Formoterol-L-tartrate form D (55% yield) (99.9% chemical purity), which contained no solvent detected by TGA analysis.

Example 16

Synthesis of (R,R)-Formoterol-L-tartrate Form D 216.7 mg (0.44 mmol) of (R,R)-arformoterol tartrate Form A were suspended in 1 mL of a mixture of methanol/water (ratio 1:1) and heated to a temperature between 60 and 70° C. for 10 min. Then, the solution obtained was allowed to cool to about 50-60° C., followed by addition of 4 mL of acetonitrile at the same temperature. Afterwards, the solution was cooled to room temperature and stirred for 1 hour. The product was collected by filtration, washed with acetonitrile and dried under vacuum (2-3 mbar, equivalent to 1.5-2.25 mm Hg) at 80° C. for 2 hours to provide 150.5 mg (69% yield) (99.92% chemical purity) of (R,R)-formoterol L-tartrate form D, which contained no solvent detected by 1H-NMR or TGA analysis.

Example 17

Synthesis of (R,R)-Formoterol-L-tartrate Form D 262 mg (0.53 mmol) of (R,R)-arformoterol tartrate Form A were suspended in 1 mL of a mixture of ethanol/water (ratio 1:1) and heated to a temperature between 60 and 70° C. for 10 min. Then, the solution obtained was allowed to cool to about 50-60° C., followed by addition of 3 mL of acetonitrile at the same temperature. Afterwards, the solution was cooled to room temperature and stirred for 1 hour. The product was collected by filtration, washed with acetonitrile and dried under vacuum (2-3 mbar, equivalent to 1.5-2.25 mm Hg) at 80° C. for 2 hours to provide 193.3 mg (74% yield) (99.94% chemical purity) of (R,R)-formoterol L-tartrate form D, which contained no solvent detected by 1H-NMR or TGA analysis.

Example 18

Synthesis of (R,R)-Formoterol-L-tartrate Form D 323.2 mg (0.65 mmol) of (R,R)-arformoterol tartrate Form A were suspended in 1 mL of a mixture of ethanol/water (ratio 1:4) and heated to a temperature between 60 and 70° C. for 10 min. Then, the solution obtained was allowed to cool to about 50-60° C., followed by addition of 3 mL of acetonitrile at the same temperature. Afterwards, the solution was cooled to room temperature and stirred for 1 hour. The product was collected by filtration, washed with acetonitrile and dried under vacuum (2-3 mbar, equivalent to 1.5-2.25 mm Hg) at 80° C. for 2 hours to provide 233 mg (72% yield) (99.94% chemical purity) of (R,R)-formoterol L-tartrate form D, which contained no solvent detected by 1H-NMR or TGA analysis.

Example 19

Synthesis of (R,R)-Formoterol-L-tartrate Form D 215.5 mg (0.44 mmol) of (R,R)-arformoterol tartrate Form A were suspended in 1 mL of a mixture of isopropanol/water (ratio 1:1) and heated to a temperature between 60 and 70° C. for 10 min. Then, the solution obtained was allowed to cool to about 50-60° C., followed by addition of 3 mL of acetonitrile at the same temperature. Afterwards, the solution was cooled to room temperature and stirred for 1 hour. The product was collected by filtration, washed with acetonitrile and dried under vacuum (2-3 mbar, equivalent to 1.5-2.25 mm Hg) at 80° C. for 2 hours to provide 130 mg (60% yield) of (R,R)-formoterol L-tartrate form D, which contained no solvent detected by 1H-NMR or TGA analysis.

Example 20

Synthesis of Form D of (R,R)-Formoterol L-tartrate, Using Arformoterol Base as Starting Material A solution of 4.2 g (28 mmol) of L-tartaric acid and 21 mL of water was added to a solution of 9.7 g (28 mmol) of arformoterol base, 70 mL ethanol and 105 mL acetonitrile at 60° C. Afterwards, the resulting mixture was seeded with form D cooled at 23° C. and stirred at this temperature for 1 hour. It was then further cooled to 0-5° C. for 1 hour and the product collected by filtration and dried under inlet air (atmospheric pressure) at 40° C. for 16 hours to provide 12.2 g (88% yield) (99.9% chemical purity, containing 0.05% of the degradation impurity (R)-1-(3-amino-4-hydroxyphenyl)-2-[[(1R)-2-(4-methoxyphenyl)-1-methylethyl]amino]ethanol) of form D of (R,R)-formoterol L-tartrate, as an off white powder, containing less than 1% of Polymorph A. 1H-NMR (200 MHz, d6-DMSO) δ: 1.03 (d, 3H); 2.50-2.67 (m, 5H); 3.72 (s, 3H); 3.99 (s, 2H); 4.65-4.85 (m, 1H); 6.82-7.15 (m, 5H); 8.02 (s, 1H); 8.28 (s, 1H); 9.60 (s, NH).

Example 21

Synthesis of a Mixture of Form D and Polymorph a of (R,R)-Formoterol L-tartrate, Using Arformoterol Tartrate Polymorph a as Starting Material 318.4 mg (0.64 mmol) of (R,R)-arformoterol tartrate Form A were suspended in 1 mL of a mixture of methanol/water (ratio 4:1) and heated to a temperature between 60 and 70° C. for 10 min. Then, the solution obtained was allowed to cool to about 50-60° C., followed by addition of 3 mL of acetonitrile at the same temperature. Afterwards, the solution was cooled to room temperature and stirred for 1 hour. The product was collected by filtration, washed with acetonitrile and dried under vacuum (2-3 mbar, equivalent to 1.5-2.25 mm Hg) at 80° C. for 2 hours to provide 278.8 mg (88% yield) (99.65% chemical purity) of a mixture of form D and polymorph A of (R,R)-formoterol L-tartrate, which contained no solvent detected by 1H-NMR or TGA analysis.

Characterisation Examples

Solubility of (R,R)-Formoterol-L-tartrate Form D

Different amounts of (R,R)-Formoterol-L-tartrate form A, B, C or D, and a mixture of forms A and D, were weighed separately and 0.5 mL of milliQ water were added. The suspensions obtained were stirred at 25° C. for 1 hour in a Crystal 16 equipment, which included a turbidity detection system that allowed determining if a solute had dissolved completely. The results obtained showed a concentration range, wherein the minor value indicated the highest concentration at which the solute dissolved completely, and the major value indicated the lowest concentration at which solute did not completely dissolve. The results are summarized in Table 1. Depending on the exact methods by which the various arformoterol tartrate polymorphs were prepared, a range of particle sizes and degrees of crystallinity were observed. The particle size ($d_{50}$ value; i.e. the median diameter) was generally found to range from 1 to 100 μm. As a result of the variation in particle size and degree of crystallinity, however, a range of different solubilities were observed for each given polymorph, as reported below.

According to The United States Pharmacopeia, 24th ed., it can be defined that form A and form B are sparingly soluble in water, while, significantly, new form D is soluble in water.

TABLE 1

Solubility assays of different polymorphic forms of (R,R)-Formoterol-L-tartrate

| (R,R)-Formoterol-L-tartrate polymorphic form | Solubility range (mg/mL) | Solubility as described in U.S. Pat. No. 6,268,533 (mg/mL) |
| --- | --- | --- |
| form A | 14-17 | 15.4 |
| form B | 24-32 | 26.7 |
| form C | 12-18 | |
| form D | 38-83 | |
| Mixture form A/form D | 14-17 | |

Stability of (R,R)-Formoterol-L-tartrate Form D and Acetonitrile Solvate of (R,R)-Formoterol-L-tartrate Stability assays of (R,R)-Formoterol-L-tartrate form D and an acetonitrile solvate of (R,R)-Formoterol-L-tartrate obtained as described above were performed at different conditions of temperature (T=5-7° C. and room temperature) after 7, 18, 30 and 90 days. The samples were placed in a vial under atmospheric pressure, under vacuum and under inert atmosphere. The results are shown in Table 2 and prove that form D is stable.

TABLE 2

Stability assays of (R,R)-Formoterol-L-tartrate form D and acetonitrile solvate of (R,R)-Formoterol-L-tartrate

| | Stability test conditions | | | | | | | | | |
|---|---|---|---|---|---|---|---|---|---|---|
| | Atmospheric pressure, Temp = 5-7° C. | | | Atmospheric pressure at room Temp | | | Inert atmosphere at room Temp | | Vacuum at room Temp | |
| Example | after 7 days | after 30 days | after 90 days | after 18 days | after 30 days | after 90 days | after 30 days | after 90 days | After 30 days | after 90 days |
| 15 | form D | form D | form D | form D | form D | form D | form D | form D | form D | form D |
| 13 | acetonitrile solvate | acetonitrile solvate | acetonitrile solvate | | | | | | | |

The invention claimed is:

1. A polymorphic form of arformoterol tartrate, designated as form D, which is characterized by at least one of the following:
   (i) a powder X-ray diffraction pattern having peaks at 6.8, 13.3, 13.6, 13.8, 14.1, 18.2, 18.7, 20.0±0.2 degrees two theta; or
   (ii) a DSC thermogram showing an endothermic peak with an onset at approximately 119-120° C., and a maximum at approximately 129-131° C., followed by an exothermic peak with a maximum at approximately 137-138° C.; wherein the DSC thermogram of form D has a further endothermic peak with an onset at approximately 168-170° C.

2. The polymorphic form of arformoterol tartrate form D according to claim 1, which has a powder X-ray diffraction pattern further comprising one or more additional peaks at 7.4, 15.9, 25.1 and 25.8±0.2 degrees two theta.

3. The polymorphic form of arformoterol tartrate form D according to claim 1, having a powder X-ray diffraction pattern in accordance with FIG. 1.

4. A mixture of form D and polymorph A of arformoterol tartrate, having at least 30% (w/w) of form D.

5. The mixture of form D and polymorph A according to claim 4, having between 40 and 50% of the known polymorph A.

6. A process for preparing arformoterol tartrate form D from arformoterol base, the process comprising the steps of:
   a) providing a mixture of arformoterol base with an alcohol, or with a combination of acetonitrile and an alcohol, at a temperature between 15 and 60° C.;
   b) adding a solution of L-tartaric acid in a solvent selected from an alcohol, water and mixtures thereof, to the mixture obtained in step (a);
   c) cooling the mixture of step (b) to a temperature between 30 and 15° C., when necessary, followed by stirring to obtain a solid;
   d) further cooling the mixture of step (c) to a temperature between 0 and 10° C.; and
   e) collecting the crystals obtained in step (d), and drying the crystals under inlet air pressure and at a temperature between 30 and 50° C. to yield arformoterol tartrate form D.

7. The process according to the claim 6, wherein the mixture provided in step (a) is a mixture of arformoterol base with an alcohol, selected from methanol, ethanol, or isopropanol; preferably methanol or ethanol; more preferably methanol.

8. The process according to claim 6, wherein the solution used in step (b) is a solution of L-tartaric acid in an alcohol, selected from methanol, ethanol, or isopropanol; preferably methanol or ethanol; more preferably methanol.

9. The process according to the claim 6, wherein the alcohol used in steps (a) and (b) is the same and is selected from methanol, ethanol and isopropanol.

10. The process according to claim 9, wherein the preferred alcohol used in step (a) and/or step (b) is methanol or ethanol.

11. The process according to claim 6, wherein the ratio of the alcohol/acetonitrile used in step (a) is of at least 1:0.1, preferably between 1:1 and 1:5.

12. The process according to claim 6, wherein the mixture of step (a) is preferably at a temperature between 20 and 60° C.

13. The process according to claim 6, wherein the temperature of the cooling carried out in step (d) is preferably between 0 and 5° C.

14. A process for the preparation of a mixture of form D and polymorph A of arformoterol tartrate, optionally from other polymorphic forms of arformoterol tartrate, and comprising the steps of:
   a) providing a mixture of arformoterol tartrate and a solvent which is a mixture of an alcohol and water, at a temperature between 60 and 70° C.;
   b) cooling the mixture obtained in step (a) to a temperature between 50 and 55° C.;
   c) adding acetonitrile to the mixture obtained in step (b) until a suspension is obtained;
   d) cooling the suspension obtained in step (c) while stirring to a temperature between 10 and 30° C. to obtain a solid; and
   e) collecting the crystals obtained in step (d) and drying the crystals under vacuum at a pressure between 0.75 and 40 mm Hg and at a temperature between 50 and 90° C.;
   wherein the ratio of alcohol:water used in step (a) is over 1:1 and up to 5:1, wherein the mixture of form D and polymorph A of arformoterol tartrate so prepared is according to claim 4.

15. A pharmaceutical composition comprising the arformoterol tartrate according to claim 1 and at least one pharmaceutically acceptable excipient or carrier.

16. A method of effecting bronchodilation, the method comprising the administration, to a subject in need of such treatment, of a therapeutically effective amount of arformoterol tartrate according to claim 1.

17. A method of effecting bronchodilation, the method comprising the administration, to a subject in need of such treatment, of a pharmaceutical composition according to claim 15.

18. The mixture of form D and polymorph A according to claim 4 having from 40% to 90% (w/w) of polymorphic form of arformoterol tartrate form D relative to the total weight of form D and polymorph A.

19. The mixture of form D and polymorph A according to claim 5 having from 50% to 80% (w/w) of polymorphic form of arformoterol tartrate form D relative to the total weight of form D and polymorph A.

* * * * *